(12) United States Patent
Clark

(10) Patent No.: US 6,280,396 B1
(45) Date of Patent: Aug. 28, 2001

(54) APPARATUS AND METHOD FOR MEASURING BODY COMPOSITION

(75) Inventor: Kenyon E. Clark, Rancho Sante Fe, CA (US)

(73) Assignee: American Weights and Measures, San Diego, CA (US)

( * ) Notice: Subject to any disclaimer, the term of this patent is extended or adjusted under 35 U.S.C. 154(b) by 0 days.

(21) Appl. No.: 09/322,001

(22) Filed: May 28, 1999

Related U.S. Application Data

(60) Provisional application No. 60/095,465, filed on Aug. 3, 1998.

(51) Int. Cl.[7] .................................................. A61B 5/05
(52) U.S. Cl. ............................................................ 600/547
(58) Field of Search .................................. 600/547, 506, 600/507, 587; 73/433; 702/50

(56) References Cited

U.S. PATENT DOCUMENTS

| | | | |
|---|---|---|---|
| 5,335,667 | * 8/1994 | Cha et al. | 600/547 |
| 5,449,000 | * 9/1995 | Libke et al. | 600/547 |
| 5,840,042 | * 11/1998 | Arpadi et al. | 600/547 |

* cited by examiner

Primary Examiner—George Manuel
(74) Attorney, Agent, or Firm—Michael de Angeli

(57) ABSTRACT

A body composition analyzer comprises a pair of handgrips extending laterally from either side of a housing containing other components of the device. Each handgrip comprises two electrodes positioned to make contact with a subject's hands when grasped. A source of low voltage, high frequency alternating current is connected across first electrodes on each handgrip, so as to form a circuit passing through the subject's body, and an impedance measuring instrument is connected to the second electrodes on each handgrip, to measure the impedance of the body in the circuit. The instrument also comprises a keypad for receiving data entered manually by the subject defining physical characteristics such as age, gender, height, weight, and the general physical condition of the subject. The input data is used to select one of a set of coefficients developed by regression analysis for use in an equation relating total body water to the impedance value and to the subject's total body water content.

38 Claims, 3 Drawing Sheets

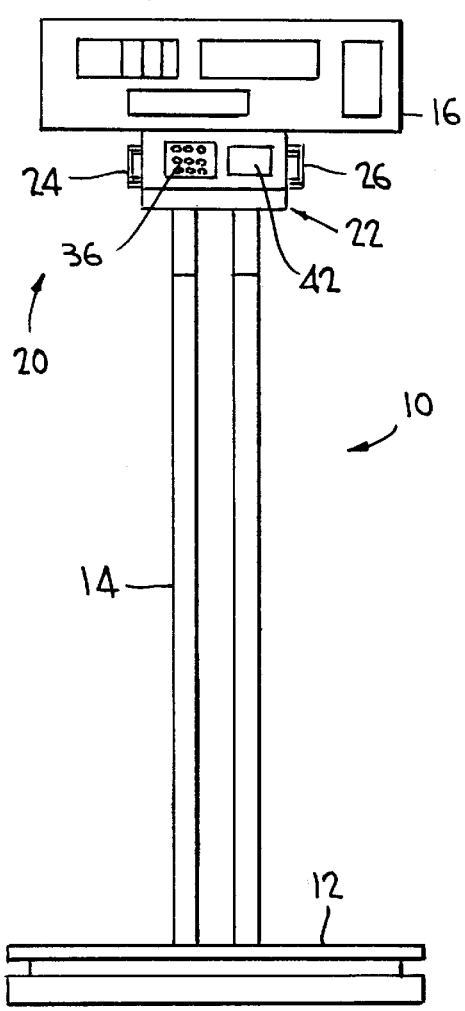
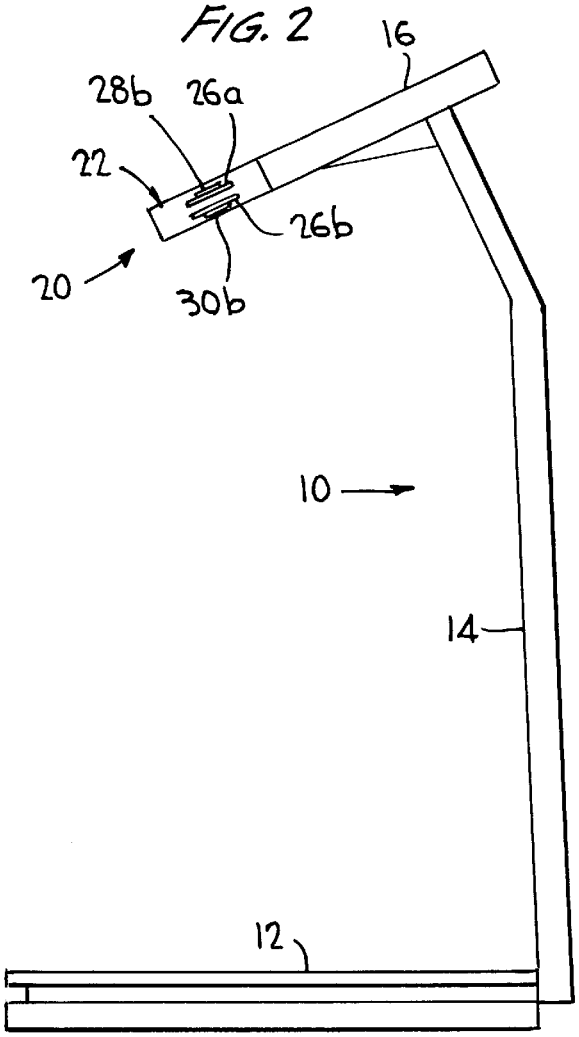
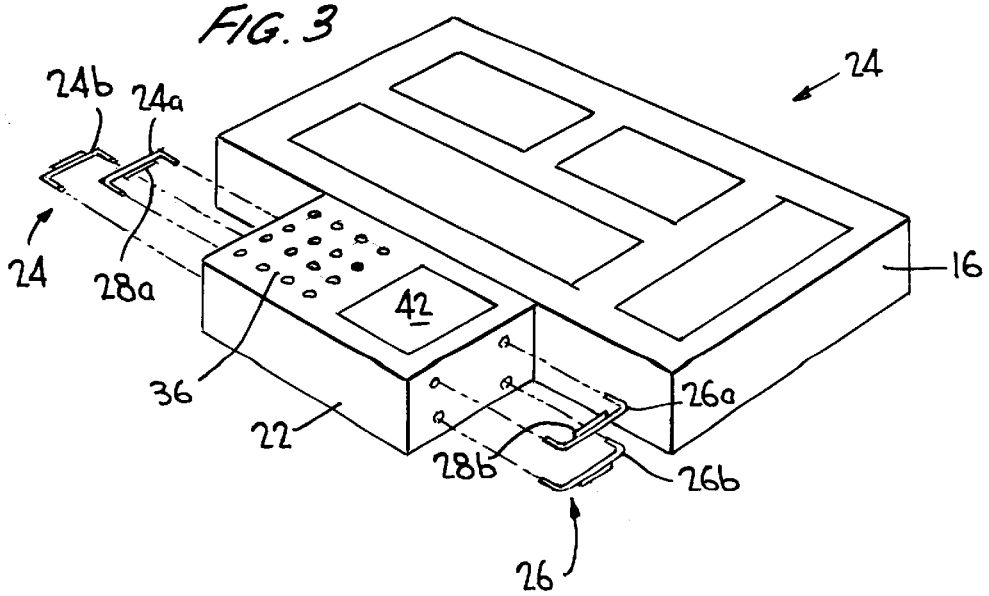

APPARATUS AND METHOD FOR MEASURING BODY COMPOSITION

CROSS REFERENCE TO RELATED APPLICATION

The present application claims priority from Provisional Patent Application Ser. No. 60/095,465, filed Aug. 3, 1998 for Apparatus and Method for Measuring Body Composition.

FIELD OF THE INVENTION

This invention relates generally to the assessment of body composition, and more particularly to a device and method for determining the weight and percentage of lean mass and fat in the body of a subject, based on determination of the total body water content of the subject's body, in turn determined by measurement of the impedance of the subject's body.

BACKGROUND OF THE INVENTION

Body composition is the distribution of body weight between lean body mass and body fat. Body composition analysis is used to define the condition of obesity, and provides useful diagnostic data for the treatment of a number of chronic conditions such as diabetes mellitus. Moreover, body composition analysis provides a method for monitoring the effects of diet and exercise.

Hydrostatic weighing has been the method of choice for assessing body composition. The subject is weighed while submerged in a tank of water, after expelling as much air from the lungs as possible. Comparison of the weight of the subject while immersed to the weight of the subject in air allows determination of body density without the complex step of measuring the amount of water displaced. After determination of the density of the body of the subject, the percentage of fat is determined by assuming constant densities of fat mass (0.9 g/cc) and lean mass (1.1 g/cc). Although considered quite accurate, the hydrostatic method of assessing body composition is burdensome, expensive, and inconvenient, and frequently cannot be applied to elderly, weak, or ill subjects.

The method of assessing body composition most often used by physicians in office settings has been measurement of skin fold thickness with calipers. Even when performed by a skilled practitioner, and after averaging the values from, for example, three measurements at each of seven different skin fold sites, the repeatability and reliability of caliper results is not good and the procedure itself is frequently uncomfortable for the subject.

Other proposed techniques of assessing body composition have included isotope dilution, near infra-red and dual energy x-ray imaging, and measurement of fat-soluble gases; each of these involve cost and/or accuracy issues not yet satisfied.

An indirect method for estimating body composition based on the measurement of electrical impedance across a portion of the subject's body has become widespread and accepted. Electrodes are effectively connected to the subject's body at two separated points and a low-voltage, high-frequency alternating current signal is passed through a circuit including that portion of the subject's body. The impedance of the body is measured and used to provide an indication of body composition, as follows.

Electrical conduction in the human body is related to the relative quantity of water and electrolytes available to carry the signal. Lean body mass (including muscle, bone, cartilage, tendons and the like) is about 75% water, generally rich in conductive ions, while fat is only about 3 to 7% water. Consequently the electrical conductivity of the lean mass is much greater than that of fat; accordingly, measurement of the body's overall impedance provides an indication of the relative ratio of the fat and lean constituents, and thus of the body composition.

Conventionally, the measured impedance is used as input to one or a set of regression equations derived from a data base of impedance values measured with subjects of known body composition, typically having been measured using the hydrostatic densitometry technique discussed above. The regression equations generally include weight and height as variables. More sophisticated models may also include gender. Less commonly, body type or morphology is included. The measured value for the impedance is also dependent on the circuit path through the body, as defined by the placement of the electrode contacts used to introduce the current and to measure the impedance. Most commonly these electrode sites have been near the wrist on one hand and near the ankle on one foot, although other electrode placements have been used.

Prior art describing variations on this basic technique include U.S. Pat. Nos. 4,947,862 to Kelly, U.S. Pat. No. 5,449,000 to Libke et al, and U.S. Pat. No. 5,720,296 to Cha. These references all show wrist-to-ankle current pathways; accurate measurements require the subject to have fasted for a set length of time prior to measurement, to have voided shortly prior, and to assume a prone or supine position with at least one foot exposed. These inconveniences are necessary for accurate measurement of impedance because fluid anomalies in the abdomen can cause false readings. Obviously the inconvenience of such constraints greatly limits the use of the technique and the market for devices implementing the technique.

U.S. Pat. No. 5,611,351 assigned to the Tanita Corporation discloses a body circuit passing from one foot to the other while the subject stands on a weighing scale. Although this overcomes some of the problems associated with wrist-to-ankle measurement, the measured impedance is still subject to lower abdomen fluid concentration anomalies and the difficulty of short circuiting if the subject's thighs touch.

Finally, in U.S. Pat. Nos. 5,579,782 and 5,817,031, both assigned to the Omron Corporation, a hand-held bio-electric impedance device is described wherein the subject grasps a portable impedance analyzer that measures hand-to-hand impedance, which is then related to body composition.

OBJECTS OF THE INVENTION

It is therefore an object of the invention to provide a body composition analysis device and method that is both accurate and convenient for the subject.

It is a further object of the invention to provide a body composition analysis device and method combining accurate measurement of a subject's weight with an assessment of body composition that is sensitive to a wide range of subject-specific characteristics, and suitable for a variety of environments, such as doctor's offices, health clubs, physical therapy and rehabilitation centers, and the like.

It is a further object of the invention to provide a body composition analyzer suitable for easy adaptation to existing fitness equipment.

It is yet another object of the invention to provide the serious body builder with a body composition analysis tool that is optimized specifically for his or her body type.

SUMMARY OF THE INVENTION

In a first embodiment, the body composition analyzing device of the invention, broadly speaking, comprises a pair of handgrips extending laterally from either side of a housing containing other components of the device, and mounted on and in electrical communication with an electronic weight scale. Each hand grip comprises two electrodes positioned to make contact with a subject's hands when grasped. A source of low voltage, high frequency alternating current is connected across first electrodes on each handgrip, so as to form a circuit passing through the subject's body, and an impedance measuring instrument is connected to the second electrode on each handgrip, to measure the impedance of the body. The instrument also comprises a keypad or like input device for receiving "subject-specific data" entered manually by the subject, for example, data defining physical characteristics such as age, gender, height, and the specific physical condition of the subject. The keypad is connected to a controller configured to receive such input data, as well as the "measured data", in this case the impedance signal and the subject's weight. The "subject-specific data" entered manually is used to select one of a set of coefficients developed by regression analysis for use in an equation relating total body water content to the impedance value measured; this information, when combined with the "measured data", is sufficient to determine the subject's total body water content. This can readily be converted to a value for total body fat content; thus the result is body composition information specifically tailored to the subject's demographic segment. This information is provided on a display, which is also used to prompt the subject to enter the "subject-specific data".

In another embodiment, the housing, to which the handgrips are mounted, is mounted to the upright beam of a physician's-style balance beam scale; in this embodiment the subject's weight is also input by way of the keypad. The display and keypad or like device for entering the "subject-specific data", the current source, the impedance measuring circuit, and the controller may be provided in the same or a separate physical unit; communication therebetween may be effected by wire or by wireless communication, for example, by infrared connection.

In alternative embodiments the body composition analyzer may be provided in generally modular form, for convenient attachment to a variety of health care or exercise equipment for convenient use in homes or gyms. In these embodiments the subject must have previously measured his weight for manual input to the processor.

Other aspects of the invention are discussed more fully below.

BRIEF DESCRIPTION OF THE DRAWINGS

The invention will be better understood if reference is made to the accompanying drawings, wherein:

FIG. 1 represents a front view of one embodiment of the body composition analyzer of the present invention, in combination with an electronic weight scale;

FIG. 2 is a side view of the body composition analyzer of the present invention in the embodiment of FIG. 1;

FIG. 3 is a perspective view of the body composition analyzer of the invention, showing the handgrips in exploded view for clarity;

DESCRIPTION OF THE PREFERRED EMBODIMENTS

A first embodiment 10 of the body composition analyzer according to the invention is shown in FIGS. 1 and 2. In this embodiment, the body composition analyzer of the invention comprises a microprocessor-based controller device 20 for determining body composition in response to subject-specific input data and measurement of the impedance of the subject's body, in combination with and mounted on and connected to an electronic weighing scale, so as to provide convenient and error-free input of the subject's weight.

Figure 5:
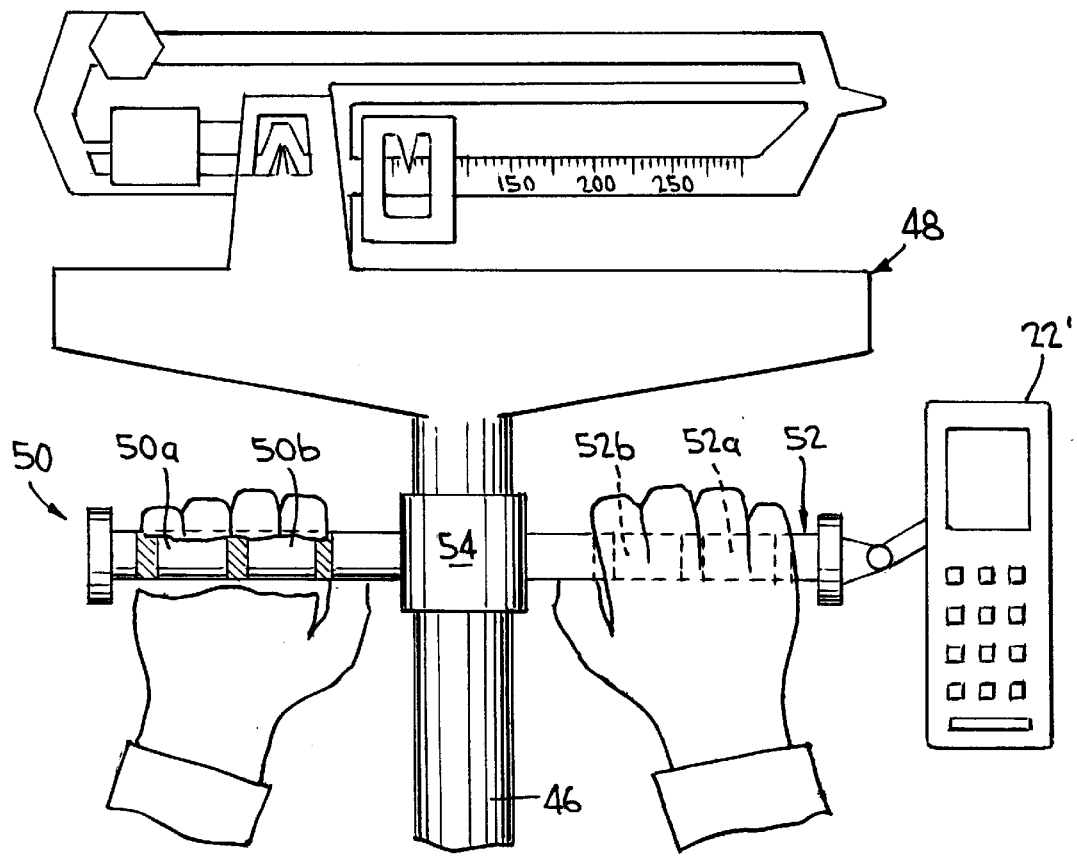
FIG. 5 shows an alternative embodiment, wherein the analyzer is mounted on a balance-beam physician's weight scale, and illustrates an alternate embodiment of the electrodes as well.

The weighing scale consists of a conventional digital readout scale comprising a base 12, a support column 14 and a head assembly 16. The controller 20 of the body composition analyzer 10 (see FIG. 3) is attached to head assembly 16, as shown, or alternatively to column 14, and comprises a controller module 22 to which are mounted opposed handgrips 24 and 26. In this embodiment handgrips 24 and 26 each comprise a pair of U-shaped electrodes 24a and 24b, and 26a and 26b, attached to the left and right sides of the control module, respectively. The handgrips can also be mounted on column 14 or head assembly 16; an alternative form for the handgrips and electrodes is shown by FIG. 5. The pairs of handgrips are positioned so that both handgrips on each side can be comfortably gripped by the subject, and so that good contact is made between the pair of electrodes on each and two spaced points on each of the subject's hands.

In the embodiment of FIGS. 1 and 2, and as further shown in FIG. 3, left handgrip pair 24 consists of two closely spaced U-shaped bars, a proximal (relative to the front of the scale) bar 24a and a distal bar 24b; similarly, right handgrip pair 26 consists of a proximal bar 26a and a distal bar 26b spaced to be simultaneously gripped by the subject's right hand. One bar of each pair forms one of the electrodes for connection of the high frequency signal, that is, for signal connection, and the other bar forms one of the electrodes for measurement of the impedance of the body of the subject that is, for signal measurement. The bars are spaced to be simultaneously gripped by the left hand of a subject using the analyzer; typically the proximal bar 24a will be gripped between the thumb and palm and the distal bar 24b by the fingertips.

The control module 22 includes a source of pulsed high frequency low voltage alternating current 32. Typically the signal is pulsed at 2–100 Hz, to reduce emissions and power consumption, and the impedance is measured between pulses. Accordingly, a large number of impedance measurements can be made in the space of a few seconds; typically the controller requires that ten readings all within 10 ohms of one another must be made before the average value thereof will be accepted as accurate. As typical impedance measurements are in the range of 300–600 ohms, this represents an approximate accuracy of +/−5 1.5–3%. The pulsed signal is in the range of 500 to 1000 microamperes at 50KHz, and passes between distal electrodes 24b and 26b and through the body of the subject. The controller comprises essentially conventional electrical impedance measurement circuitry 34 (FIG. 4) connected to proximal electrodes 24a and 26a to measure the subject's body impedance.

As shown in FIG. 3, the control module 22 also includes an input keypad 36 and a display screen 42. The controller includes a microprocessor 40 (FIG. 4) programmed in known fashion to control the operation of the body composition analyzer of the invention. Specifically, in the preferred embodiment, the microprocessor controls operation of display screen 42 so as to prompt the subject (or an aide or physician) to enter "subject-specific" data, specifically age, gender, height, an indication of whether the subject is clothed or not, and the physical condition of the subject, by way of keypad 36. Other prompting and data entry devices, such a touch-screen display combining functions of keypad and display, are within the scope of the invention as well. In the embodiment of FIGS. 1 and 2, the subject's weight is communicated directly from the scale head 16 to the controller; in other embodiments, the weight information is also input manually by way of the keypad 36.

Figure 4:
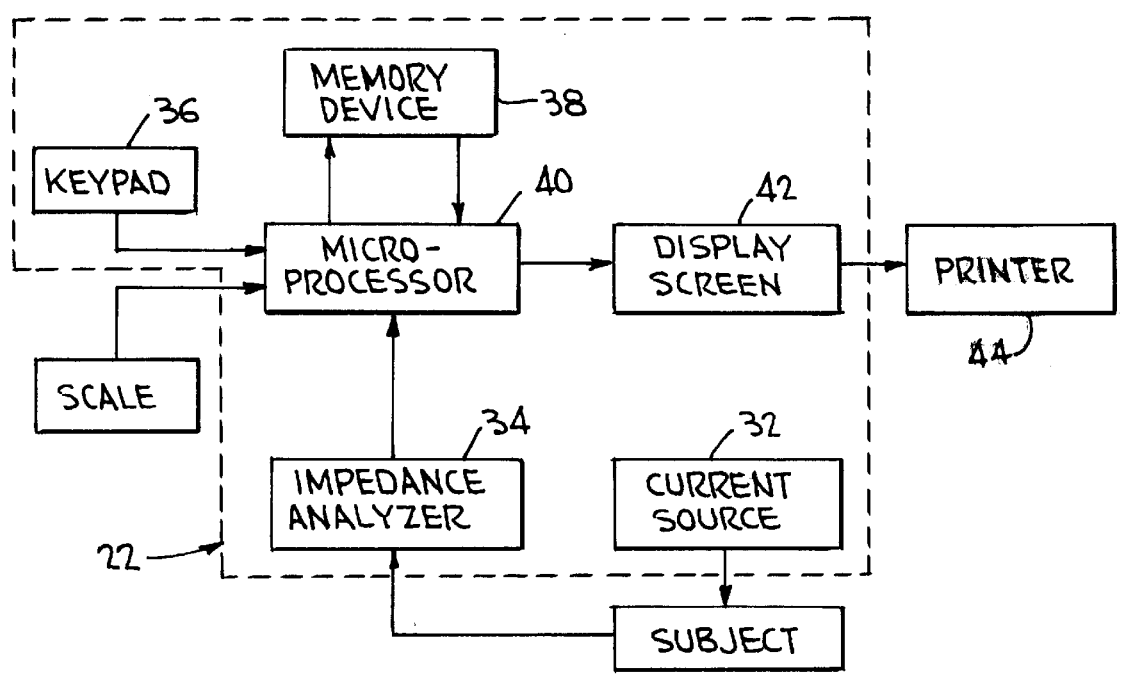
FIG. 4 is a block diagram of the controller of the body composition analyzer of the present invention, and shows its connection to other elements of the device.

With further reference to FIG. 4, it can be seen that the controller further comprises a memory device 38. Memory device 38 stores a data base comprising the sets of coefficients determined from regression analysis of segmented sample population data; one set of coefficients corresponds to each of a large number of sample populations. For example, in the embodiment discussed in detail herein, the subject's physical condition is assumed to fall into one of four categories, that is, the obese, persons of normal physical condition, athletes, and body builders, and the subject's age is characterized as within one of six age groups, that is, prepubescent, adolescent, young adult, adult, middle aged, and elderly. The subject's gender is also used to select a set of coefficients, such that a total of at least 48 (4 physical types ×6 age groups ×2 genders) sets of coefficients are stored in the memory device 38 as the database.

The memory device may also be used for storing the body composition-impedance relationship equation to which the coefficients are applied in determining any particular subject's total body water content, as well as microprocessor "firmware" or "microcode"; these may also be stored in a separate memory device. The microcode provides the program according to which a microprocessor 40 employs the input data and the measured impedance, together with the equation and selected coefficients, to produce a body composition analysis. The microcode is also used by the microprocessor to control the other functions of the analyzer according to the invention, such as operating the display so as to prompt the subject to enter the required input data, accepting this data (and the weight data if provided by way of an associated electronic scale), controlling the transmission of the high-frequency signal into the subject's body and the measurement of the responsive impedance value, performing the corresponding calculation, and displaying the result on display screen 42. An optional printer 44 can be connected to the microprocessor to provide the subject with a hard copy of the results and, also optionally, health and fitness data, suggestions, and warnings as may be appropriate based on the results. FIG. 4 shows a functional flow diagram of information into and out of control module 22. Implementation of the functions described for the microprocessor and associated equipment is within the skill of the art given the functional description hereof.

The equation employed according to this invention to calculate the total body water content of a subject is parametrized with respect to a particular subject in accordance with a unique regression analysis subdivision of the subject population, as indicated above. That is, the method of analysis of total body water content of the invention is responsive not only to the conventionally measured hand-to-hand impedance value, and the weight and height parameters associated with many of the prior art approaches, but also to the age, gender, and physical condition of the subject.

The form of the equation employed according to this invention to calculate the total body water content of a subject is:

$$TBW=(C1*H^2/Z)+(C2*(Wt-cw))+C3;$$

wherein:

TBW is Total Body Water, in liters;

C1, C2, and C3 are regression coefficients corresponding to different population segments categorized by age, gender, and the physical condition of the subject;

Wt is the Weight of the subject, in pounds;

cw is an estimated value of clothing weight (3.5 lbs for females; 4.5 lbs for males);

H is the Height of the subject: and

Z is the measured impedance.

The specified input age, gender, and physical condition data is used by the controller to determine which of a number of population segments best matches the body characteristics of the subject. More specifically, in response to input data thus characterizing the subject, a set of coefficients C1, C2, and C3 are selected from sets of coefficients stored by memory device 38. The stored coefficients having been determined by comparison of hydrostatic body-density measurement carried out on subjects of the various populations to impedance measurements also having been carried out thereon using the methods described above, a positive correlation is thus provided between the impedance measurements and the well-established hydrostatic measurements.

FIG. 5 shows a further embodiment of the invention, wherein the controller is integrated with a balance beam weighing scale 48 in lieu of the electronic scale of the FIGS. 1–3 embodiment. As indicated at 54, the entire body composition analyzer can be clamped onto the upright stanchion 46 of the scale without modification thereof. In this embodiment, the subject's measured weight value is provided to the controller 22' by keypad entry rather than through direct input to microprocessor 36. An alternative configuration for the controller 22' is illustrated; the functions are essentially as described above. An alternative handgrip and electrode configuration also shown in FIG. 5 includes the use of non-vertical single bar handgrips 50 and 52, each having a pair of electrodes, 50a and 50b and 52a and 52b, respectively disposed thereon and separated by an insulator. FIG. 5 also shows that the handgrips can be mounted on a mounting structure separate from the housing of the controller. The handgrips and electrodes can take various shapes to better suit the ergonomics of the target populations.

Figure 6:
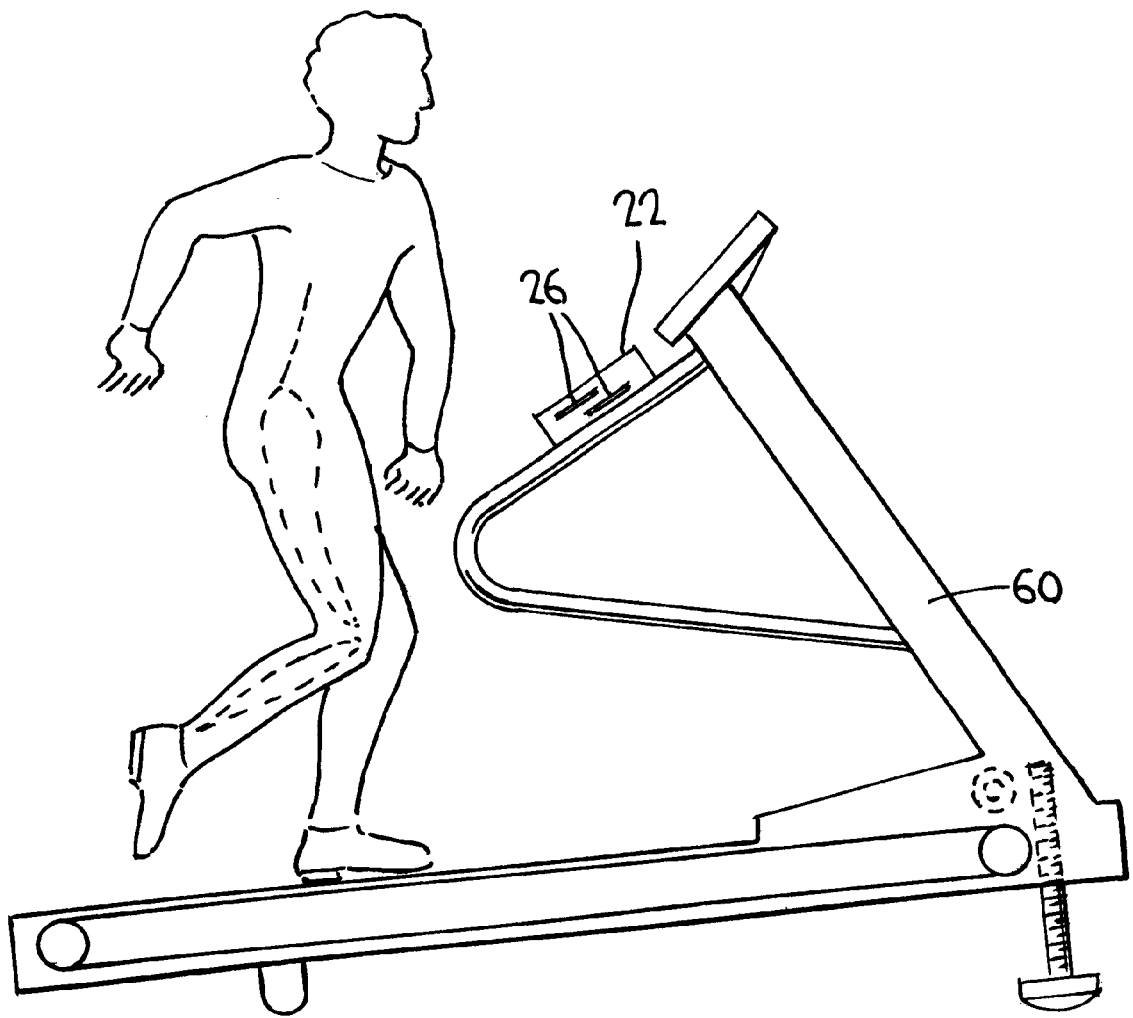
FIG. 6 shows a schematic view of the controller of the body composition analyzer of the present invention, in combination with an exercise apparatus, a treadmill in the embodiment shown.

The body composition analyzer according to the invention can also be attached to various health/fitness/aerobic exercise equipment. FIG. 6 shows a controller 22 generally according to the FIGS. 1–3 embodiment of the invention mounted on a treadmill 50. The user can conveniently check body water content before and after a workout. It might be thought that sweat between the subject's skin and the electrodes would lead to false readings, but this is not so; the high-frequency current and impedance signals are efficiently transmitted through even marginal contact between dry skin and the electrodes, such that the presence of sweat, albeit an excellent conductor, does not add significantly to the contact between the subject and the electrodes. Similarly, the alternative current path that might be thought to be formed by sweat on the subject's skin does not interfere with the measurement. The body composition analyzer according to the invention can similarly be attached to other exercise apparatus, including but not limited to stair-step machines, exercise bicycles, elliptical weight-training systems, and cross-training equipment; the electrodes can also be used for other diagnostic and evaluation purposes, such as monitoring the subject's pulse rate.

In use of the body composition analyzer according to the invention, referring to the FIGS. 1–3 embodiment, the subject is prompted to enter gender, age, height H, physical condition, and clothing input data into the microprocessor 40 through the control console keypad 36. The subject then assumes an upright position on the scale 10, facing the head assembly 16, and extends his hands forward to grasp the handgrips, 24 and 26, establishing electrical contact with the four electrodes 24a, 24b, 26a, and 26b. Pulses of low voltage, low current, high frequency alternating current are applied by the current source 32 to the distal electrodes 24b and 26b, and flow from the subject's hands through the upper portion of the subject's body; providing this current path essentially avoids the potentially misleading fluid accumulations typical of the lower torso.

Concurrently the measured weight Wt of the subject, adjusted by a clothing weight factor cw when appropriate, is transmitted by the scale head 16 to the microprocessor 40, and the impedance, Z, of the subject's body is measured across the proximal electrodes, 28a and 28b, by the electrical impedance analyzer 34, and these values are also transmitted to the microprocessor 40.

Based on the age, gender, and physical condition input data, the subject is assigned to a population segment of individuals having similar characteristics, and the appropriate set of coefficients C1, C2, and C3, developed by regression analysis of the body composition results obtained by hydrostatic weighing or other reliable techniques with respect to this population segment, is selected and applied to the fundamental equation, again:

$$TBW=(C1*H^2/Z)+(C2*(Wt-cw))+C3$$

where the notation is as before. The result is an estimate of the subject's total body water content correlated with respect to similar results made with respect to individuals of similar body type, age, and gender.

The resultant value for total body water content is displayed to the subject on display screen 42; this value can be converted to a value for total body fat content as follows. The fat-free mass of the subjects' body, "FFM", is equivalent to the total body water content, TBW, divided by a coefficient C4 that varies with the gender and age of the subject, thus:

$$FFM=TBW/C4$$

where

C4=0.751 for males of ages 10–15 years
C4=0.725 for males of ages 16–39 years
C4=0.718 for males of ages 40+ years
C4=0.772 for females of ages 10–15 years
C4=0.758 for females of ages 16–39 years
C4=0.741 for females of ages 40+ years The fat content FC of the subject's body is then simply determined by:

$$FC=(Wt-FFM)/Wt$$

where Wt is the subject's weight, as above.

Optionally a printout including basic fitness information, suggestions and warnings can be provided by optional printer 44.

Finally, in the event it proves desirable to charge a fee for use of the instrument of the invention, this can be implemented reliably by incorporating a modem in the unit, connected to the microprocessor, and supplying the unit with a "count", that is, a number stored in memory corresponding to a prepaid number of tests. As the unit is employed to make measurements as above, the count is decremented; when it reaches a relatively low number of remaining tests, the operator is prompted to arrange for replenishment in exchange for a payment, much in the manner of postage meter updating as now provided.

While a preferred embodiment of the invention has been shown and described in detail, together with various contemplated alternative embodiments, it will be appreciated that there are various further modifications and improvements that can be made without departure from the spirit and scope of the invention.

I claim:

1. A body composition analyzer for determining the total body water content of a subject, comprising:
    a mounting structure;
    first and second pairs of electrodes, said pairs of electrodes being mounted on opposite lateral sides of said mounting structure, and disposed for simultaneous gripping of both pairs of electrodes by a subject;
    means for supplying a high frequency alternating current signal across one of said first pair of electrodes and one of said second pair of electrodes, so that said signal passes through the body of the subject;
    means for measuring the impedance of the body of the subject across the second of said first pair of electrodes and the second of said second pair of electrodes, and for providing an impedance signal responsive thereto; and
    a controller for receiving input information including at least the height, weight, gender, and general physical condition of the subject, and for processing said impedance signal responsive to said input information to determine the total body water content of the subject; wherein
    said body composition analyzer is integrated with an electronic weighing scale and receives said input information concerning the weight of the subject directly from said scale.

2. The body composition analyzer according to claim 1, wherein said body composition analyzer is integrated with an electronic weighing scale such that when the subject stands on said scale, said electrodes extend in front of said subject for convenient gripping.

3. The body composition analyzer according to claim 1, wherein said controller processes said impedance signal to determine total body water content for a particular subject by selecting a set of coefficients from a group of sets of coefficients, each set of coefficients representing the result of a regression analysis performed on the body density-impedance relationship of a particular population segment, wherein the particular set of coefficients selected with respect to a particular subject are selected in response to said input information including at least the height, gender, and general physical condition of the subject.

4. The body composition analyzer according to claim 3, wherein said regression analysis is represented by an equation of the form:

$$TBW=(C1*H^2/Z)+(C2*(Wt-cw))+C3;$$

wherein:
TBW is Total Body Water content of the subject;
C1, C2 and C3 are regression coefficients corresponding to different population segments categorized by age, gender, and physical condition of the subject;
Wt is the Weight of the subject;
cw is an estimated value of clothing weight;
H is the Height of said subject: and
Z is the measured impedance.

5. The body composition analyzer according to claim 4, wherein the regression coefficients corresponding to the physical condition of the subject are selected responsive to identification of the subject as a member of one of four population segments identified as the obese, persons of normal physical condition, athletes, and body builders.

6. The body composition analyzer according to claim 4, wherein the regression coefficients corresponding to the age of the subject are selected responsive to determination that the subject's age indicates membership in one of six age categories: prepubescent, adolescent, young adult, adult, middle aged, and elderly.

7. The body composition analyzer according to claim 1, wherein said controller includes means for receiving input as to the height, gender, and general physical condition of the subject manually through a keypad.

8. The body composition analyzer according to claim 1, wherein said controller includes means for conversion of the calculated value for total body water content to a value for total body fat content.

9. A body composition analyzer for determining the total body water content of a subject, comprising:
a mounting structure;
first and second pairs of electrodes, said pairs of electrodes being mounted on opposite lateral sides of said mounting structure, and disposed for simultaneous gripping of both pairs of the electrodes by a subject;
means for supplying a high frequency alternating current signal across one of said first pair of electrodes and one of said second pair of electrodes, so that said signal passes through the body of the subject;
means for measuring the impedance of the body of the subject across the second of said first pair of electrodes and the second of said second pair of electrodes, and for providing an impedance signal responsive thereto; and
a controller for receiving input information including at least the height, weight, gender, and general physical condition of the subject, and for processing said impedance signal responsive to said input information to determine the total body water content of the subject; and
wherein said controller processes said impedance signal to determine total body water content for a particular subject by selecting a set of coefficients from a group of sets of coefficients, each set of coefficients representing the result of a regression analysis performed on the body density-impedance relationship of a particular population segment, and the particular set of coefficients selected with respect to a particular subject being selected in response to said input information including at least the height, gender, and physical condition of the subject.

10. The body composition analyzer according to claim 9, wherein the result of said regression analysis is represented by an equation of the form:

$$TBW=(C1*H^2/Z)+(C2*(Wt-cw))+C3;$$

wherein:
TBW is Total Body Water content of the subject;
C1, C2 and C3 are regression coefficients corresponding to different population segments categorized by age, gender and physical condition of the subject;
Wt is the Weight of said subject;
cw is an estimated value of clothing weight;
H is the Height of said subject: and
Z is the measured impedance.

11. The body composition analyzer according to claim 9, wherein the regression coefficients corresponding to the physical condition of the subject are selected responsive to identification of the subject as a member of one of four population segments identified as the obese, persons of normal physical condition of the subject, athletes, and body builders.

12. The body composition analyzer according to claim 9, wherein the regression coefficients corresponding to the age of the subject are selected responsive to determination that the subject's age indicates membership in one of six age categories: prepubescent, adolescent, young adult, adult, middle age, and elderly.

13. The body composition analyzer according to claim 9, wherein said controller includes means for receiving input as to the height, gender, and physical condition of the subject manually through a keypad.

14. In combination, the body composition analyzer according to claim 9, and a weighing scale.

15. The combination of claim 14, wherein said scale is an electronic weighing scale, and wherein said controller is connected to said scale so as to receive said input information concerning the weight of the subject directly from said scale.

16. The combination of claim 14, wherein said weighing means is a balance beam weighing scale.

17. The combination of claim 16, wherein said pairs of electrodes are provided as exposed portions of opposed handgrips extending laterally outwardly from said mounting structure having been affixed to a central upright member of said balance beam weighing scale, for convenient gripping by a subject.

18. In combination, the body composition analyzer according to claim 9, and an exercise apparatus, wherein said body composition analyzer is mounted by said mounting structure to said exercise apparatus such that a subject may conveniently grasp said pairs of electrodes while performing exercises according to the normal function of the exercise apparatus.

19. The combination of claim 18, wherein said exercise apparatus is selected from the group including: treadmills, stair-step machines, exercise bicycles, elliptical weight-training systems, and cross-training equipment.

20. The body composition analyzer according to claim 9, wherein said controller includes means for conversion of the calculated value for total body water content to a value for total body fat content.

21. In combination, an exercise apparatus whereby a subject may perform a specific biomechanical exercise, and a body composition analyzer for determining the total body water content of a subject, said body composition analyzer comprising:

a mounting structure;

first and second pairs of electrodes, said pairs of electrodes being mounted on opposite lateral sides of said mounting structure, and being disposed for simultaneous gripping of both pairs of the electrodes by a subject;

means for supplying a high frequency alternating current signal across one of said first pair of electrodes and one of said second pair of electrodes, so that said signal passes through the body of the subject;

means for measuring the impedance of the body of the subject across the second of said first pair of electrodes and the second of said second pair of electrodes, and for providing an impedance signal responsive thereto; and a controller for receiving input information including at least the height, weight, gender, and general physical condition of the subject, and for processing said impedance signal responsive to said input information to determine the total body water content of the subject; and wherein said controller processes said impedance signal to determine body fat content for a particular subject by selecting a set of coefficients from a group of sets of coefficients, each set of coefficients representing the result of a regression analysis performed on the body density-impedance relationship of a particular population segment, and the particular set of coefficients selected with respect to a particular subject being selected in response to said input information including at least the height, gender, and general physical condition of the subject; and wherein said body composition analyzer is mounted by said mounting structure to said exercise apparatus such that a subject may conveniently grasp said pairs of electrodes while performing exercises according to the function of the exercise apparatus.

22. The combination of claim 21, wherein said exercise apparatus is selected from the group including: treadmills, stairstep machines, exercise bicycles, elliptical weight-training systems, and cross-training equipment.

23. The combination of claim 21, wherein said controller includes means for conversion of the calculated value for total body water content to a value for total body fat content.

24. The combination of claim 21, wherein the result of said regression analysis is represented by an equation of the form:

$$TBW=(C1*H^2/Z)+(C2*(Wt-cw))+C3;$$

wherein:

TBW is Total Body Water content of the subject;

C1, C2 and C3 are regression coefficients corresponding to different population segments categorized by age, gender and physical condition of the subject;

Wt is the Weight of said subject;

cw is an estimated value of clothing weight;

H is the Height of said subject: and

Z is the measured impedance.

25. The combination of claim 21, wherein the regression coefficients corresponding to the physical condition of the subject are selected responsive to identification of the subject as a member of one of four population segments identified as the obese, persons of normal general physical condition, athletes, and body builders.

26. The combination of claim 21, wherein the regression coefficients corresponding to the age of the subject are selected responsive to determination that the subject's age indicates membership in one of six age categories: prepubescent, adolescent, young adult, adult, middle age, and elderly.

27. The combination of claim 21, wherein said controller includes means for receiving input as to at least the age, height, gender, and physical condition of the subject manually through a keypad.

28. A body composition analyzer for measuring the total body water content of a subject, said body composition analyzer comprising:

a housing for containing components of said body composition analyzer;

first and second pairs of electrodes, said pairs of electrodes being mounted on opposite lateral sides of said housing, and being disposed for simultaneous gripping of both pairs of the electrodes by a subject;

means for supplying a high frequency alternating current signal across one of said first pair of electrodes and one of said second pair of electrodes, so that said signal passes through the body of the subject;

means for measuring the impedance of the body of the subject across the second of said first pair of electrodes and the second of said second pair of electrodes, and for providing an impedance signal responsive thereto; and a controller for receiving input information including at least the height, weight, gender, and general physical condition of the subject, and for processing said impedance signal responsive to said input information to determine the total body water content of the subject; and wherein said controller processes said impedance signal to determine total body water content for a particular subject by selecting a set of coefficients from a group of sets of coefficients, each set of coefficients representing the result of a regression analysis performed on the body density-impedance relationship of a particular population segment, and the particular set of coefficients selected with respect to a particular subject being selected in response to said input information including at least the height, gender, and physical condition of the subject, and wherein the regression coefficients corresponding to the physical condition of the subject are selected responsive to identification of the subject as a member of one of four population segments identified as the obese, persons of normal general physical condition of the subject, athletes, and body builders.

29. The body composition analyzer of claim 28, wherein the result of said regression analysis is represented by an equation of the form:

$$TBW=(C1*H^2/Z)+(C2*(Wt-cw))+C3;$$

wherein:

TBW is Total Body Water content of the subject;

C1, C2 and C3 are regression coefficients corresponding to different population segments categorized by age, gender and general physical condition of the subject;

Wt is the Weight of said subject;

cw is an estimated value of clothing weight;

H is the Height of said subject: and

Z is the measured impedance.

30. The body composition analyzer of claim 29, wherein the regression coefficients corresponding to the age of the subject are selected responsive to determination that the subject's age indicates membership in one of six age categories: prepubescent, adolescent, young adult, adult, middle age, and elderly.

31. The body composition analyzer of claim 28, wherein said controller includes means for receiving input as to the age, height, gender, and general physical condition of the subject manually through a keypad.

32. The body composition analyzer of claim 28, wherein said controller further includes means for conversion of the calculated value for total body water content to a value for total body fat content.

33. The body composition analyzer of claim 28, wherein said controller further includes means for maintaining a count of the number of analyses performed relative to a fixed number of analyses having been authorized, and means for adding additional authorized analyses upon payment therefor.

34. A method for estimating total body water content of the body of a subject, comprising the steps of:

1) providing a controller for:
   a) accepting input data for categorizing the subject according to the parameters of gender, age, and general physical condition;
   b) accepting input data descriptive of the subject's height and weight;
2) transmitting a high frequency alternating current signal into the body of the subject at first spaced contact points;
3) measuring the impedance of the body of the subject responsive to said current signal between second spaced contact points on the body of the subject; and
4) employing said controller to calculate the total body water content of the subject according to the equation:

$$TBW = (C1*H^2/Z) + (C2*(Wt-cw)) + C3;$$

wherein:

TBW is Total Body Water;

C1, C2 and C3 are coefficients selected responsive to said input data concerning the gender, age, and physical condition of the subject;

Wt is the Weight of the subject;

cw is an estimated value of clothing weight;

H is the Height of said subject; and

Z is said measured impedance; and wherein said coefficients are selected from sets of coefficients developed by regression analysis of comparison of prior body composition measurement results, said prior body composition measurement results having been obtained by hydrostatic weighing or other accepted total body water measurement techniques performed with respect to populations parametrized according to gender, age, and physical condition of the members of the populations, with impedance measurements of the total body water content of said members.

35. The method of claim 34, wherein said first and second spaced contact points are located on the right and left hands of the subject.

36. The method of claim 35, wherein said controller is physically integrated and in signal communication relation with an electronic weighing scale, and wherein said step of accepting input data descriptive of the subject's weight is performed by direct communication of said data from said scale to said controller.

37. The method of claim 34, wherein said steps of accepting input data for categorizing the subject according to the parameters of gender, age, and physical condition, and accepting input data descriptive of the subject's height, are implemented using a keypad comprised by said controller.

38. The method of claim 34, comprising the further step of converting said calculated value for the total body water content of said subject to a value for the total fat content of the body of said subject.

* * * * *